US006859519B2

(12) United States Patent
Neumann

(10) Patent No.: US 6,859,519 B2
(45) Date of Patent: Feb. 22, 2005

(54) METHOD AND SYSTEM FOR ANALYZING DIFFRACTION DATA FROM CRYSTALLINE SYSTEMS

(75) Inventor: Marcus A. Neumann, Chatou (FR)

(73) Assignee: Accelrys Software Inc., San Diego, CA (US)

( * ) Notice: Subject to any disclaimer, the term of this patent is extended or adjusted under 35 U.S.C. 154(b) by 75 days.

(21) Appl. No.: 10/444,852

(22) Filed: May 22, 2003

(65) Prior Publication Data

US 2004/0039533 A1 Feb. 26, 2004

Related U.S. Application Data

(60) Provisional application No. 60/383,763, filed on May 24, 2002.

(51) Int. Cl.[7] ............................................. G01N 23/207
(52) U.S. Cl. ........................................... 378/75; 378/73
(58) Field of Search ............................... 378/70, 71, 73, 378/75

(56) References Cited

U.S. PATENT DOCUMENTS

| | | | | |
|---|---|---|---|---|
| 4,892,721 A | * | 1/1990 | Leonowicz et al. | ......... 423/705 |
| 5,366,718 A | * | 11/1994 | Sato et al. | ............... 423/594.1 |
| 6,341,257 B1 | | 1/2002 | Haaland | |
| 2002/0183861 A1 | | 12/2002 | McRee et al. | |

OTHER PUBLICATIONS

Altomare, et al., "New Techniques for Indexing: N–TREOR in EXPO" (2000) Applied Crystallography, vol. 33 pp. 1180–1186.

Boultif, et al., "Indexing of Powder Diffraction Patterns for Low–Symmetry Lattices by the Successive Dichotomy Method" (1991) J. Appl. Cryst., vol. 24 pp. 987–993.

Werner, et al., "TREOR, a Semi–Exhaustive Trial–and–Error Powder Indexing Program for all Symmetries." (1985) J. Appl. Cryst., vol. 18 pp. 367–370.

Kohlbeck, et al., "Trial and Error Indexing Program for Powder Patterns of Monoclinic Substances." (1978) J. Appl. Cryst., vol. 11 pp. 60–61.

Visser, "A Fully Automatic Program for Finding the Unit Cell from Powder Data" (1969) J. Appl. Cryst., vol. 2 pp. 89–95.

Taupin, "A Powder–Diagram Automatic–Indexing Routine" (1973) J. Appl. Cryst., vol. 6 pp. 380–385.

Shirley, R. (1999). <http://www.ccp14.ac.uk/tutorial/crys/program/crysfire.htm>.

* cited by examiner

*Primary Examiner*—David V Bruce
(74) *Attorney, Agent, or Firm*—Knobbe Martens Olson & Bear LLP

(57) ABSTRACT

A method and system for indexing powder diffraction data are disclosed comprising choosing a maximum impurity peak tolerance level for a crystallography data search, choosing a range of number of calculated peaks for possible indexing solutions having a minimum number of peaks and a maximum number of peaks, selecting a crystal system to search, selecting powder extinction classes to search for indexing solutions, performing an exhaustive unit cell search of each of the selected powder extinction classes using a successive dichotomy approach to determine a set of indexing results, and ranking the obtained solutions according to likelihood.

14 Claims, 3 Drawing Sheets

METHOD AND SYSTEM FOR ANALYZING DIFFRACTION DATA FROM CRYSTALLINE SYSTEMS

CROSS REFERENCE TO RELATED APPLICATIONS

This application claims priority under 35 U.S.C. Section 119(e) to U.S. Provisional Application Ser. No. 60/383,763 entitled Method and System for Analyzing X-Ray Diffraction Data and filed on May 24, 2002. The entire disclosure of the No. 60/383,763 application is hereby incorporated by reference in its entirety.

BACKGROUND OF THE INVENTION

1. Field of the Invention

The invention relates generally to the field of crystallography and specifically to the field of analysis of powder diffraction data.

2. Description of the Related Art

Crystal structure determination from powder diffraction data is an active field of current research because of the difficulties involved in growing single crystals of many compounds. Two key steps of the structure determination process are known as indexing and structure solution. In indexing, unit cell parameters are derived from the reflection positions, whereas structure solution focuses on the determination of atomic coordinates from the reflection intensities. With the recent development of direct space algorithms for structure solution, indexing has emerged as a new important bottleneck for crystal structure determination from powder diffraction data.

Most indexing algorithms take reflection positions as input. Prior to indexing, these peak positions have to be extracted from the powder diffraction pattern, which extraction inevitably results in a loss of information, particularly in the case of strong peak overlap. It may, therefore, seem desirable to use full-profile-comparison instead of comparing extracted and calculated peak positions. Full-profile-comparison, however, is computationally demanding, and a complete unit cell search based on full-profile comparison would require huge amounts of CPU resources even for today's standards.

Various strategies have been implemented in a variety of programs to solve the indexing problem. The three indexing programs most commonly in use, ITO (Visser 1969), TREOR (Eriksson & Westdahl, 1985) and DICVOL (Boultif & Louër, 1991), each adopt rather different approaches.

ITO first establishes a list of possible zones in reciprocal space. In a second step, zones with a common axis are combined and the angle between them is determined. The program FJZN6 (Shirley, 1999) is a modified version of the ITO zone-indexing program. TREOR belongs to the category of trial & error algorithms, together with KOHL (Kohlbeck & Hörl, 1978), TAUP (Taupin, 1973) and the more recent implementation n-TREOR (Altomare et al., 2000). Trial & error algorithms tentatively assign hkl indices to as many low angle peaks as there are unknown lattice parameters. Many different peak selections and assignments of hkl indices are tried, and for each choice a trial cell is calculated using a simple matrix inversion, or other equivalent methods. The reflections belonging to the trial cell are then compared to the full list of experimentally observed peak positions. The search is carried out for each crystal system separately.

A completely different approach, known as a successive dichotomy method, is used by DICVOL. For each crystal system, the space of possible unit cells is divided into small volume elements that are searched one by one in the order of increasing cell volume. Since each volume element corresponds to a range of unit cell parameters, a range of possible positions can be calculated for each reflection. These peak ranges are then compared to the experimentally observed peak positions, taking into account experimental errors. If one or more of the experimentally observed peaks are not covered by any of the calculated ranges, the entire volume element is rejected. Otherwise, the volume element is cut into smaller sub-volumes and the whole procedure is repeated. After a certain number of recursions, the cell corresponding to the remaining volume element is accepted as a potential indexing solution. In the programs LZON and LOSHFZRF (Shirley & Louër, 1978), the successive dichotomy method is combined with a grid search technique.

The eight indexing programs described above have fairly different strengths and weaknesses. It is not uncommon that some of them succeed in solving a given problem, while others fail. To increase the overall chance of success, indexing with all eight algorithms is carried out automatically by the CRYSFIRE suite (Shirley, 1999). While this approach certainly has its merits, it is by no means equivalent to an exhaustive and systematic search of the space of possible unit cells.

A new approach has recently been described (Kariuki et al., 1999) that uses a genetic algorithm in conjunction with full-profile comparison. As has been pointed out above, a major drawback of full-profile comparison is the computational cost involved, even if the profile function is first fitted to a couple of isolated low angle peaks and then kept constant throughout the simulation. Additional difficulties occur in cases where the profile parameters vary significantly over the range of the diffraction pattern due to particle size broadening, lattice strain broadening or experimental factors.

Despite past efforts to solve the indexing problem, the failure rate of the most commonly used indexing algorithms is fairly high, and it is important to understand the reasons why existing indexing algorithms frequently fail. Among the more obvious reasons is zero-point shift, a constant offset of the experimentally observed peak positions. If the zero-point shift is too large, it needs to be taken into account explicitly or indexing is impossible. Some of the programs described above address this problem by using an external loop over different values of the zero-point shift.

Another reason for failure is the presence of impurity peaks, which are reflections that cannot be attributed to the unit cell of the main crystalline phase and, therefore, remain unindexed. The robustness with respect to impurity peaks is quite different for the various indexing algorithms. For example, a single impurity peak is sufficient in most cases to make indexing with DICVOL impossible.

In some cases, indexing fails because of restrictions on the covered search space. For instance, many indexing algorithms stop once a solution is found that has a figure of merit, a measuring criteria describing the quality of the solution, above a certain threshold and the correct solution may never be reached. Another example is by DICVOL's use of default ranges for the unit cell volume and the unit cell lengths and angles. If the correct unit cell falls outside these ranges, which cannot be known beforehand, the default settings need to be changed.

A more subtle reason for failure is related to the presence of a dominant zone. In the case of flat unit cells, all reflections up to a certain 2-theta value or down to a certain d-spacing belong to a single zone in reciprocal space. In extreme cases, only reflections belonging to the dominant zone may be selected for indexing, and it is impossible to find the correct unit cell if the presence of a dominant zone is not recognized and taken into account.

Finally, there is one more reason that is rarely addressed. Due to strong peak overlap, preferred orientation or poor statistics, a high ratio of reflections may not be observed experimentally and accurate peak positions for the observed peaks may be difficult to obtain. In such cases, which occur rather frequently in an industrial working environment, the correct unit cell is difficult to distinguish from a large number of incorrect solutions with similar figures of merit.

SUMMARY OF THE INVENTION

The systems and methods have several features, no single one of which is solely responsible for its desirable attributes. Without limiting the scope as expressed by the claims that follow, its more prominent features will now be discussed briefly. After considering this discussion, and particularly after reading the section entitled "Detailed Description of the Preferred Embodiments" one will understand how the features of the system and methods provide several advantages over traditional systems and methods.

In one aspect, a method of indexing powder diffraction data from a crystalline sample obtained using a radiation source such as x-rays, neutrons, or electrons (simply referred to as "powder diffraction data" in this document), is disclosed wherein the method comprises:

choosing a maximum impurity peak tolerance level to limit the search for indexing solutions to those where the number of unindexed peaks lies within the tolerance level.

choosing a range for the number of calculated peaks to limit the search for indexing solutions to those where the number of calculated peaks falls within the chosen range., Selecting a Powder Extinction Class to Search Performing an exhaustive unit cell search of the selected powder extinction class using a successive dichotomy approach to determine a set of indexing results.

In another aspect, a method is described for exploiting space group symmetry in the indexing of powder diffraction data, by selecting a crystal system to search, then grouping possible indexing solutions compatible with this crystal system into powder extinction classes having the same pattern of systematic absences, and performing separate indexing solution searches within at least two of said powder extinction classes, up to the maximum of powder extinction classes compatible with the selected crystal system In yet another aspect, a system is described for indexing a set of powder diffraction data, comprising a general purpose processor adapted to divide the data into a plurality of powder extinction classes having the same pattern of systematic absences. The processor is further adapted to search each powder extinction class for solutions where the calculated peak number falls within a given range.

In another aspect, another system is described for indexing a set of powder diffraction data, comprising a memory adapted to store data and a processor. Wherein the processor is adapted to read data from and write data to the memory and is further adapted to execute functions on the data. The processor is further adapted to search said data for indexing solutions starting at solutions with a small number of calculated peaks and progress toward solutions with a larger number of calculated peaks.

In another aspect, yet another system is described for ranking and comparing indexing solutions for powder diffraction data corresponding to different extinction classes using a figure of merit designed to rank highly the most likely indexing solutions, i.e., solutions with small numbers of calculated peaks and small numbers of impurity peaks.

In another aspect, yet another system is described for indexing powder diffraction data, comprising means for choosing a maximum impurity peak tolerance level to limit the search for indexing solutions for powder diffraction data to those where the number of unindexed peaks lies within the tolerance level, means for choosing a range for the number of calculated peaks to limit the search for indexing solutions to those where the number of calculated peaks falls within the chosen range., means for selecting a crystal system to search, means for selecting the powder extinction classes to search for indexing solutions, and means for performing an exhaustive unit cell search of the selected powder extinction classes using a successive dichotomy approach to determine a set of indexing results. The system may further include means for ranking the collection of solutions according to a figure of merit designed to rank highly the most likely solutions.

DETAILED DESCRIPTION OF THE PREFERRED EMBODIMENT

Figure 1:
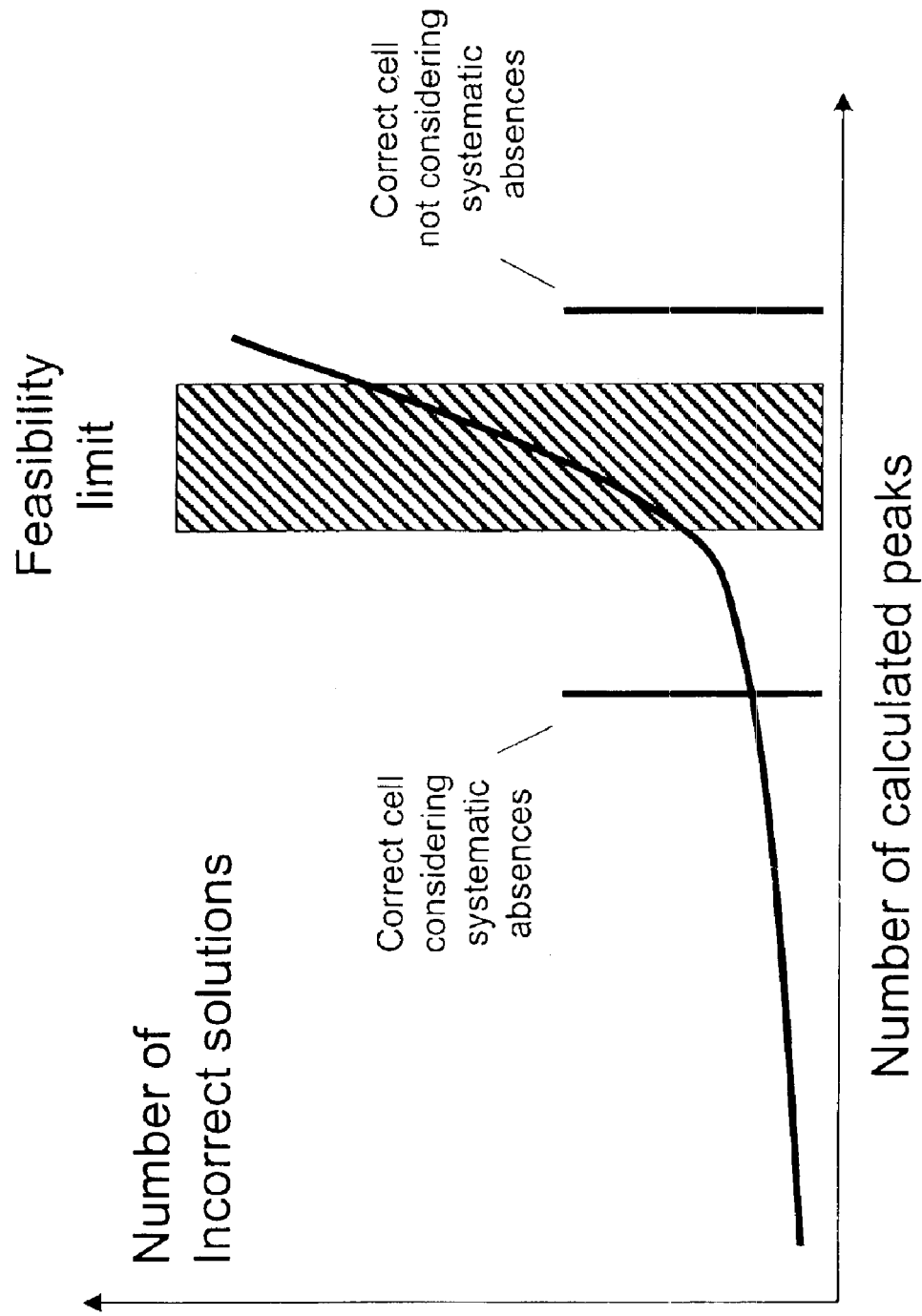
FIG. 1 is a schematic graph representing the number of indexing solutions that result in a set of peaks matching a given set of experimental peaks, as a function of the number of calculated peaks. As the number of calculated peaks increases, the likelihood of solutions that accidentally match the set of experimental peaks increases.

Embodiments of the invention will now be described with reference to the accompanying figures, wherein like numerals refer to like elements throughout. The terminology used in the description presented herein is not intended to be interpreted in any limited or restrictive manner simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Most indexing algorithms commonly in use have been developed more than ten years ago, when the available CPU resources were far more limited than today. At the time of their development, these algorithms provided a judicious compromise between robustness and completeness on one hand and speed on the other hand. For today's standards, however, they use only small amounts of CPU time, in the range from seconds to minutes, while they frequently fail to produce the right answers. To put these circumstances into perspective, it should be pointed out that typical calculation times during the structure solution step range from several hours to several days on state-of-the-art PCs and workstations. As indexing is a prerequisite for structure solution, it is appropriate to increase the overall chances of success by devoting more CPU resources to the indexing step.

Described herein is a novel indexing algorithm that makes intelligent use of modern computer hardware to carry out a quasi-exhaustive unit cell search.

To address the problems described above, one embodiment performs a complete search of the space of possible unit cells, going from cells with low numbers of calculated peaks to cells with high numbers of calculated peaks. Systematic absences are taken explicitly into account. A choice of impurity tolerance levels allows the user to specify the maximum number of unindexed reflections. The search is carried out in such a way that the more likely solutions are considered first. For a given peak number range, a given pattern of systematic absences (a.k.a extinction class) and a given impurity tolerance level, an exhaustive search is performed using a successive dichotomy approach. The zero-point shift is determined as part of the indexing procedure. All indexing solutions are fully optimised, compared and ranked according to a newly defined figure of merit. A multistep procedure facilitates the indexing of long and flat unit cells. Each of these features can be used in an indexing method alone or in combination with any or all of the other described features. The various features mentioned above are discussed in detail below.

A. Search from Low to High Peak Numbers

As input for indexing, it is common practice to select all clearly distinguishable diffraction peaks up to a certain 2-theta value. The list of observed diffraction peaks can only approximate the positions of theoretically expected peaks, as some peaks can be concealed by peak overlap while the intensity of others can be too low to be detected. Nevertheless, 20% or more of all symmetry allowed reflections are typically observed. The task of indexing consists of finding a unit cell for which the calculated 2-theta positions of the diffraction peaks match the experimentally observed ones. The likelihood of finding an incorrect cell that accidentally matches the observed peak positions increases as the resulting number of calculated reflections within the considered 2-theta range increases. In the limit of very high numbers of calculated peaks, most unit cells produce a match for the observed peak positions to a certain extent. As a consequence, solutions with low numbers of calculated peaks are to be preferred if several unit cells match a given peak selection equally well. It is thus also advantageous for different hkl reflections to be counted as a single calculated peak if the corresponding 2-theta positions are identical because of symmetry constraints.

Since both the volume of the search space and the number of incorrect solutions increase rapidly with the number of calculated peaks, some embodiments explore the search space going from cells with low numbers of calculated peaks to cells with high numbers of calculated peaks. The increase of the number of incorrect solutions with the number of calculated peaks is schematically depicted in FIG. 1. If the correct unit cell gives rise to a low number of calculated peaks, it is found early on in the search and, in general, easily distinguished from the few incorrect solutions with similar numbers of calculated peaks. On the other hand, if the number of calculated peaks is high, the correct unit cell may only be found after a very long time and may be lost in a mass of incorrect solutions. In between these two extremes, there is a region that is called the feasibility limit as illustrated in FIG. 1. If the correct unit cell falls into this region, it can be difficult but often is not impossible to identify. Beyond the feasibility limit, indexing may be essentially impossible.

B. Systematic Absences

In many embodiments of the invention, systematic absences are taken into account. Systematic absences are reflections whose intensities are systematically zero due to the nature of the crystal space group. The benefits associated with this are illustrated in FIG. 1. In FIG. 1, two vertical lines represent the correct unit cell. The line to the right corresponds to the case where systematic absences are neglected, meaning that absent peaks are counted as calculated reflections. If there are systematic absences and they are taken into account, meaning that the systematic absences are accounted for by removing them from the count of calculated reflections, the number of calculated reflections is thereby smaller. Consequently, this case is represented by the vertical line further to the left in FIG. 1. Considering systematic absences has two advantages. Since the search proceeds from low peak numbers to high peak numbers, the correct unit cell is found earlier on and less CPU time is required. In addition, the correct cell is less likely to be hidden among a group of many incorrect solutions. The situation depicted by the vertical line to the right of the feasibility limit in FIG. 1 corresponds to a case where the correct cell is lost beyond the feasibility limit if systematic absences are not taken into account, while it can be found if systematic absences are considered. Taking systematic absences into account can reduce the number of calculated peaks quite significantly. For centered space groups like C2, 50% or more of all reciprocal lattice vectors correspond to systematic absences.

For every crystal system other than triclinic, there are several space groups with exactly the same pattern of forbidden and allowed 2-theta positions regardless of the precise unit cell parameters. We call a set of space groups with the same pattern of allowed 2-theta positions a powder extinction class. To take systematic absences into account, the unit cell search has to be carried out independently for each powder extinction class. In total, there are 1, 6, 34, 32, 9 and 17 powder extinction classes in the triclinic, monoclinic, orthorhombic, tetragonal, hexagonal/trigonal and cubic crystal systems, respectively. It is unnecessary to consider the various space groups of a powder extinction class separately.

C. Impurity Tolerance Levels

Frequently, some of the peaks of a powder diffraction pattern do not belong to the main crystalline phase but to one or more impurity phases. Such peaks cannot be attributed to a reciprocal lattice vector of the main crystalline phase and remain unindexed. Some embodiments of the invention use explicit impurity tolerance levels that specify how many unindexed diffraction peaks are acceptable. In some embodiments, the user can select an impurity tolerance level to be used during the search. Some specific level definitions that have been found suitable in some embodiments are described below. In some embodiments, searching can be performed at the selected level, or at all levels up to the selected level.

At level 0, all experimentally observed peaks need to be indexed. At level 1, 1 unindexed peak is allowed among the first 20 observed peaks, 2 unindexed peaks are allowed among the first 40 peaks and so forth. In some embodiments there is a total of 8 different impurity tolerance levels, as illustrated in Table 1, although other impurity tolerance levels can be used and these are provided as one advantageous example that has been found suitable in one embodiment.

TABLE 1

An illustration of the number of unindexed impurity peaks allowed in a given number of observed peaks for each impurity tolerance level.

| Level | Number of impurity peaks |
|---|---|
| 0 | None |
| 1 | 1 in first 20, 2 in first 40, . . . |
| 2 | 2 in first 10, 3 in first 20, 4 in first 30 |
| 3 | 2 in first 5, 3 in first 10, 4 in first 15 |
| 4 | 2 in first 3.5, 3 in first 7, 4 in first 10.5 |
| 5 | 2 in first 2, 3 in first 4, 4 in first 6 |
| 6 | Like 4, but 2 more at low angle |
| 7 | Like 5, but 4 more at low angle |

As illustrated in Table 1, for levels 1 to 5, one additional impurity peak is allowed every 20, 10, 5, 3.5 and 2 observed peaks, respectively. Levels 2 to 5 are different from level 1 in the 2 impurity peaks are accepted among the first 10, 5, 3.5 and 2 observed peaks, respectively. It can happen that the unit cell of the impurity phase is bigger than the until cell of the main crystalline phase, so that the first few diffraction peaks at low 2-theta values all belong to the impurity phase. To account for such a case, levels 6 and 7 are like levels 4 and 5 but allow for 2 and 4 additional impurity peaks below and among the first few reflections of the dominant phase.

With increasing impurity tolerance, the likelihood of finding incorrect solutions also increases. Referring to FIG. 1, it follows that the feasibility limit shifts to the left, or towards lower numbers of calculated peaks. This observation has important implications. If all observed peaks belong to a single crystalline phase, then it is not uncommon, in such a case, that the correct unit cell can be found using a low impurity level, while it is beyond the feasibility limit if using a high impurity level. It should also be pointed out that the CPU time required to find the correct cell increases significantly with growing impurity tolerance. Thus, performing a search at a high impurity tolerance level may sometimes be necessary, but can also hamper or prevent successful indexing. To look effectively for solutions with high numbers of calculated peaks and for solutions with high numbers of unindexed peaks in a single run, some embodiments perform parallel searches at all impurity tolerance levels up to a maximum impurity tolerance level defined by the user.

D. Search Order

Figure 2:
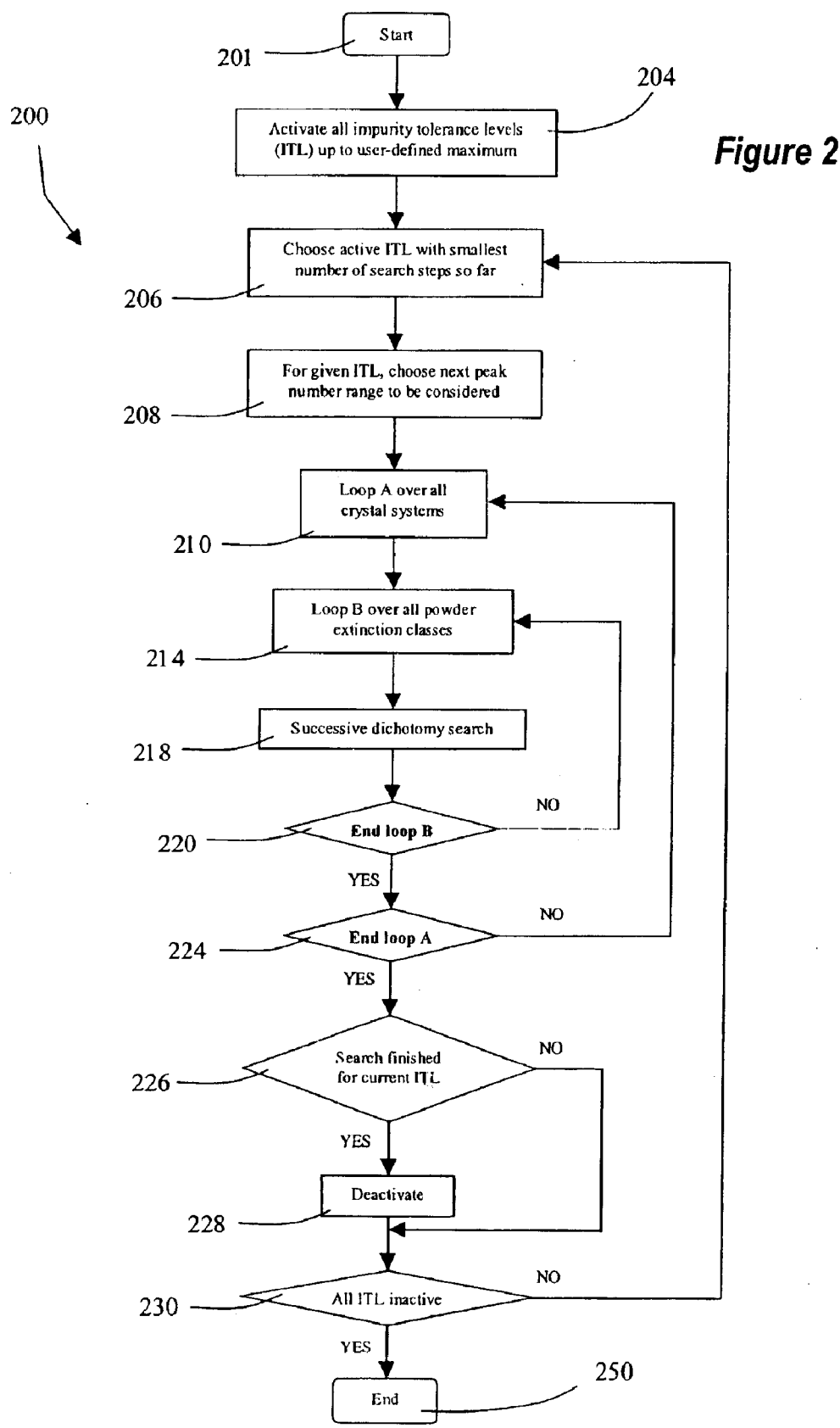
FIG. 2 is a flow chart illustrating one embodiment of a process for indexing crystallographic powder diffraction data.

It has already been mentioned that certain embodiments may perform a search at various impurity tolerance levels, going from low numbers of calculated peaks to high numbers of calculated peaks. It has also been said that a separate search is performed for each powder extinction class, using a successive dichotomy approach. Now, a description of how these different elements may work together is provided and their connection is also illustrated by the flow chart or a process 200 in FIG. 2 which is a graphic illustration of an embodiment of the process described herein. This search process 200 has been designed such that the more likely solutions are considered first and that the feasibility limit is reached at the various impurity tolerance levels at a relatively close proximity in time.

Some embodiments keep track of the computational effort invested at the various impurity tolerance levels by counting the number of dichotomy steps performed at each level. Still referring to FIG. 2, the process 200 begins at a starting state 201. The process 200 then moves to an impurity tolerance level activation state 204 where a user selects a user-defined maximum impurity tolerance level and, initially, all impurity tolerance levels, up to the user-defined maximum, are activated. The process 200 then moves to an impurity tolerance level selection state 206 where the impurity tolerance level with the lowest number of successive dichotomy search steps performed so far is selected for further searching. For the selected impurity tolerance level, a range of allowed numbers of calculated peaks is determined in a peak range determination state 208. When an impurity tolerance level is selected for the first time, the lower limit of the range is taken to be the minimum number of observed peaks that need to be indexed, which is equal to the number of observed peaks minus the maximum number of impurity peaks allowed for the chosen impurity level. At subsequent selections of the same impurity tolerance level, the lower limit is set to the previous upper limit plus 1. The width of the range, or the number of peaks in the range, roughly corresponds to 25% of the minimum number of observed peaks that need to be indexed. Having chosen an impurity tolerance level and a peak number range, the process 200 then moves to a crystal system selection state 214 where the first or next crystal system is selected for further searching. The process 200 loops over all crystal systems from trigonal/hexagonal, cubic, tetragonal, orthorhombic and monoclinic to triclinic.

For each crystal system, the process 200 then moves to a powder extinction class selection state 214 where the first or next powder extinction class in a crystal system is chosen for searching. The process 200 runs through all powder extinction classes for a crystal system individually during the searching. Finally, having selected an impurity tolerance level, a peak number range, a crystal system and a powder extinction class, the process 200 moves to a search state 218 where an exhaustive unit cell search is performed by means of a successive dichotomy approach. An example of the details of performing such a search will be discussed below. The process 200 then moves to a powder extinction class loop state 220 that checks if there are other powder extinction classes in the crystal system to search. If there are further powder extinction classes in the instant crystal system, the process 200 will return to the powder extinction class selection state 214 where the next powder extinction class is selected for searching. When there are no remaining powder extinction classes in the crystal system to be searched, the process will move to a crystal system loop state 224. At crystal system loop state 224, the process 224 determines if there are any remaining crystal systems to be searched at the current impurity tolerance level. If there are more crystal systems to be searched, the process 200 will then return to crystal system selection state 210 where the next crystal system is selected for searching. If there are no more crystal systems to be checked at the current impurity tolerance level, then the system moves to impurity tolerance level termination state 226.

Having worked through the inner loops, the process 200 moves to an impurity tolerance level termination decision state 226. Impurity tolerance level termination decision state 226 checks if further searches at higher peak ranges are required for the selected impurity tolerance level. If a set of predetermined termination criteria, to be discussed below, is reached then the impurity tolerance level will be deactivated by a deactivation state 228 and the process will move to an impurity tolerance level complete determination state 230. If the predetermined termination criteria has not been achieved, then the process 200 will skip deactivation state 228 and proceed directly to impurity tolerance levels complete determination state 230. Impurity tolerance levels complete determination state 230 determines if there are any active impurity tolerance levels remaining. If there are, the process 200 will return to impurity tolerance level selection state 206. As long as there are active impurity tolerance levels, the process 200 returns to the beginning of the external loop and selects the next impurity tolerance level to be processed. When there are no further active impurity tolerance levels the process 200 moves to an ending state 250 where the process is terminated and the results are output, if not produced during search state 218.

By counting the number of dichotomy steps, systems utilizing this process 200 can make sure that about the same amount of CPU time is spent at all impurity tolerance levels. As a consequence, the indexing of a pure phase requires about 5 times more CPU time if the search is carried out at levels 0 to 4 instead of level 0 only.

E. Successive Dichotomy

As described above, some successive dichotomy methods of indexing have been described in previous publications, and any of these previously describe methods may be used in the various embodiments described herein. It has been found, however, that computational efficiency can be improved by incorporating certain features into the approach that are described below.

The key idea of the successive dichotomy method is to divide the search space into initial volume elements and to use certain criteria to decide which volume elements can or cannot contain solutions. Unfavorable volume elements are rejected immediately, while favorable volume elements are recursively divided into smaller sub-volumes to which the same criteria are applied. Volume elements that have become small enough are accepted as indexing solutions.

In this subsection, an explanation is provided of how the total search volume is cut into initial volume elements, how volume elements are compared to the selection of observed peaks, how volume elements are cut into smaller sub-volumes in a recursive procedure, and how the recursion depth is regulated. For the sake of simplicity, the first item in this list will be discussed last, and the full discussion is limited to the triclinic crystal system. Some of the particularities to be considered in crystal systems of higher symmetry are discussed in a paragraph at the end of this subsection.

First, the task of comparing a given volume element of the search space to the list of observed reflections is described. The aim of the comparison is to determine whether or not the volume element may contain an indexing solution. The first consideration is the experimental diffraction peaks. Systems utilizing certain embodiments of the process described herein can take the $2\theta$ positions, $2\theta_i$, and the Full Width Half Maximum, $\Delta 2\theta_{FWHM,i}$, of the observed diffraction peaks as input. The $2\theta$ positions are subject to a certain experimental error, and the limiting values $2\theta_{min,i}$ and $2\theta_{max,i}$ that are supposed to bracket the real peak positions are expressed in terms of a fraction of the FWHM:

$$2\theta_{min,i}=2\theta_i-0.5*\kappa*\Delta 2\theta_{FWHM,i} \quad (1a)$$

$$2\theta_{max,i}=2\theta_i+0.5*\kappa*\Delta 2\theta_{FWHM,i} \quad (1b)$$

Initially, the system may make a rather conservative estimate and assume $\kappa=1.0$, i.e. the real peak positions fall into the intervals that corresponds to the FWHM. The effect of the zero-point shift may be neglected at this stage and will be discussed in the next subsection. For indexing, it is convenient to transform the error intervals from $2\theta$ positions to squared reciprocal d-spacings, or Q.

$$Q_{min,exp,i}=4*\sin(\theta_{min,i})/\lambda^2 \quad (2a)$$

$$Q_{max,exp,i}=4*\sin(\theta_{max,i})/\lambda^2 \quad (2b)$$

In the above equations, $\lambda$ is the wavelength of the radiation used in the measurement.

We now establish the link between the Q values and the lattice parameters. Rather than using cell lengths a, b, c and cell angles $\alpha$, $\beta$, $\gamma$, it is convenient to describe the unit cell in terms of parameters $x_1, \ldots, x_6$ that are defined as the scalar products of the reciprocal lattice vectors a*, b* and c*:

$$x_1=<a^*,a^*>,\ x_2=<b^*,b^*>,\ x_3=<c^*,c^*>, x_4=2<a^*,b^*>,\ x_5=2<a^*,c^*>, x_6=2<b^*,c^*> \quad (3)$$

The parameters $x_1, \ldots, x_6$ are related to the Q values of hkl reflections by a simple equation:

$$Q_{h\,k\,l}=h^2x_1+k^2x_2+l^2x_3+h\,k\,x_4+h\,l\,x_5+k\,l\,x_6 \quad (4)$$

In the space of triclinic cells, a volume element can be defined by the following set of conditions:

$$x_i \in [x_{i,min}, x_{i,max}]\ i=1,\ldots,6 \quad (5)$$

For the unit cells in such a volume element, there is a range $[Q_{min,\,hkl}, Q_{max,\,hkl}]$ of possible Q values for each hkl reflection:

$$Q_{min,\,hkl}=h^2x_{1,min}+k^2x_{2,min}+l^2x_{3,min}+\min(h\,k\,x_{4,min},\,h\,k\,x_{4,max})+ \min(h\,l\,x_{5,min},\,h\,l\,x_{5,max})+\min(k\,l\,x_{6,min},\,k\,l\,x_{6,max}) \quad (6a)$$

$$Q_{max,\,hkl}=h^2x_{1,max}+k^2x_{2,max}+l^2x_{3,max}+\max(h\,k\,x_{4,min},\,h\,k\,x_{4,max})+ \max(h\,l\,x_{5,min},\,h\,l\,x_{5,max})+\max(k\,l\,x_{6,min},\,k\,l\,x_{6,max}) \quad (6b)$$

In the above equations, it has been exploited that $h^2$, $k^2$, $l^2$, $x_1$, $x_2$, and $x_3$ are always positive. Using (Eq. 6a) and (Eq. 6b), the system may establish a list of Q intervals for all hkl reflections that fall into the Q range covered by the experimental reflections. The hkl reflections that have exactly the same Q values due to symmetry constrains, like (h,k,l) and (−h,−k,−l) in the triclinic case, are counted only once.

To find out if the volume element under consideration may contain an indexing solution, the list of calculated Q intervals can be compared to the Q intervals of the experimentally observed diffraction peaks. Every experimental Q interval that has no overlap with any of the calculated Q intervals corresponds to an impurity peak. If the number of confirmed impurity peaks exceeds the allowed maximum, the volume element cannot contain an indexing solution and can be rejected. Some embodiments use a rejection rule that is slightly more sophisticated that the simple criterion described above. To a limited extent, the system may take into account that each calculated Q-interval should only be attributed to a single experimental Q interval.

While the rejection of volume elements is based on more or less the same principles as previously known techniques such as DICVOL, different strategies may be employed to divide volume elements into smaller sub-volumes. DICVOL, for example, cuts each of the 6 intervals into (Eq. 5) 2 smaller parts, thus creating 64 smaller sub-volumes. Some invention embodiments also generate 64 sub-volumes in total, but individual intervals can be divided into 1, 2, 4, 8, 16, 32 or 64 parts. The numbers of parts are chosen in such a way as to lead to an early rejection of unfavorable volume elements. The basic idea behind this approach is easy to understand. For a given volume element, the calculated Q-intervals are larger and more frequent at higher Q-values. Throughout the first few recursive levels of the successive dichotomy procedure, only observed and calculated reflections at low Q-values determine rejection and acceptance of volume elements, because observed reflections at higher Q-values are virtually always matched by calculated reflections. Thus, embodiments can choose cuts that result in an advantageous reduction of the interval sizes in the low Q region. The first few calculated peaks frequently belong to a single row or zone in reciprocal space, and their positions do not depend on all of the parameters $x_1, \ldots, x_6$. The precise nature of the cut that is made depends on the average unit cell parameters within the volume element. With increasing depth of the recursion, the chosen cuts depend more and more on the interval sizes at higher Q values.

Certain embodiments also include a novel way that the maximum recursion depth is regulated. While DICVOL stops the successive dichotomy procedure after a fixed number of recursions, certain embodiments may continue until the widths of all calculated Q-intervals are smaller than the FWHM of the observed peaks with which they overlap. The approach implemented in these embodiments has the advantage that virtually all possibilities of assigning calculated to observed peaks are explicitly generated. In cases with strong peak overlap, certain embodiments will thoroughly examine the various possible assignments, since the correct solution may otherwise be left out. For all volume elements that satisfy the termination criterion of the recursive procedure, the corresponding unit cell is further optimized, minimizing the disagreement between the calculated and the experimental peak positions. As a consequence of the small-grained dissection of search space, many of these volume elements result in the same optimized unit cells. To improve the efficiency of the algorithm, it is important to limit the number of optimizations that lead to the same result, because the minimization process is fairly time consuming. To accomplish this, the number of identical solutions found can be constantly monitored. If solutions are found too often, the width of the experimental Q-intervals can then be reduced progressively by decreasing the parameter K in (Eq. 1a) and (Eq. 1b) from 1.0 to 0.1. As the Q-intervals of the observed peaks become smaller, the overlap with the calculated Q-intervals decreases and less volume elements are accepted as solutions at the deepest level of the recursion. Changes made to the parameter K are retained until a further reduction is required. For the various impurity tolerance levels, different values of K are used and adjusted independently. If, at some point throughout a unit cell search, the reduction of K is insufficient to limit the number of optimizations, a maximum recursion depth may be introduced temporarily and later removed.

Another aspect of this successive dichotomy approach is the dissection of the search space into initial volume elements. Embodiments of the invention may use a system of 6 nested loops to generate adjacent, non-overlapping intervals for each of the parameters $x_1, \ldots, x_6$. According to (Eq. 5), the combination of six of these intervals defines a volume element. The nested loops are set up in such a way that all volume elements are explicitly considered that may contain unit cells for which the number of calculated peaks falls into the allowed range. The initial volume elements correspond to a broad range of peak numbers, and the size of the ranges decreases as the volume elements are cut into smaller and smaller parts. At all levels of the recursion, the allowed peak number range may be compared to the ranges covered by individual volume elements. Volume elements with no overlap may be immediately rejected. Another consideration for the nested loops is to avoid redundancy, since triclinic unit cells can be defined in many different but equivalent ways. Some embodiments assume that a* is the shortest reciprocal lattice vector, while b* is the shortest lattice vector not collinear to a*. Finally, in these embodiments, c* is the shortest lattice vector that cannot be expressed as a linear combination of a* and b*. Using the above definition, a set of conditions can be derived for the parameters $x_1, \ldots, x_6$:

$$x_1 <= x_2 <= x_3 \tag{7a}$$

$$|x_4| <= x_1 \tag{7b}$$

$$|x_5| <= x_1 \tag{7c}$$

$$|x_6| <= x_2 \tag{7d}$$

$$x_6 >= x_4 + x_5 - x_1 - x_2 \tag{7e}$$

The parameters $x_1$, $x_2$ and $x_3$ are always positive by definition. Without loss of generality, one can choose $x_4 >= 0$ and $x_5 >= 0$. The parameter $x_6$ can be positive or negative. Only volume elements in agreement with the above conditions need to be considered.

F. Zero-point Shift

In powder diffractometry, a more or less constant offset between the observed and the ideal peak positions is frequently observed, that can be attributed to a slight misalignment of the experimental set-up, among other things. This offset, known as the zero-point shift, is determined in some embodiments along with the unit cell parameters. We define the zero-point shift $2\theta_{zp}$ in such a way that the ideal peak positions are the difference of the observed peak positions $2\theta_i$ and the zero point shift.

$$2\theta_{ideal,i} = 2\theta_i - 2\theta_{zp} \tag{8}$$

In general, the zero-point shift falls within a small interval $[2\theta_{zp,min}, 2\theta_{zp,max}]$ around zero, where typical values for $2\theta_{zp,min}$ and $2\theta_{zp,max}$ are $\pm 0.1°$. The zero-point shift adds to the uncertainty of the real peak positions, and (Eq. 1a) and (Eq. 1b) become:

$$2\theta_{min,i} = 2\theta_i - 0.5 * \kappa * \Delta 2\theta_{FWHM,i} - 2\theta_{zp,max} \tag{9a}$$

$$2\theta_{max,i} = 2\theta_i + 0.5 * \kappa * \Delta 2\theta_{FWHM,i} - 2\theta_{zp,min} \tag{9b}$$

The possible range of values for the zero-point shift increases the uncertainty of the real peak positions substantially, thus reducing the ability to distinguish between correct and incorrect indexing solutions. It is therefore advantageous to split the full range of possible values into smaller intervals. At first sight, it may seem tempting to include the zero-point shift in the dichotomy procedure in analogy with the unit cell parameters. However, it has to be kept in mind that (Eq. 2a & 2b) used to transform the 2θ intervals into Q intervals involve the evaluations of sinusoidal functions. Therefore, recalculating the observed intervals at every step of the successive dichotomy procedure would be very time consuming and a different approach may be implemented.

The zero-point shift is associated with the observed Q intervals, whereas the unit cell parameters are related the calculated Q intervals. The full range of possible zero-point shifts, $[2\theta_{zp,min}, 2\theta_{zp,max}]$, is divided into smaller parts, and a complete set of observed Q-intervals may be calculated and stored for all of the sub-intervals as well as for the full range. The sub-intervals can be ordered in such a way that sub-intervals close to the center of the full range come first.

In some embodiments, when a volume element has to be compared to the observed peak positions, a first comparison is performed using the observed Q-intervals for the full range $[2\theta_{zp,min}, 2\theta_{zp,max}]$. If the calculated and observed Q-intervals don't match, the volume element is rejected. Otherwise, the comparison is repeated for the first sub-interval and, if no match is obtained, for subsequent subintervals. If all sub-intervals fail to give a positive result, the volume element is rejected. Otherwise, the evaluation of subsequent subintervals is stopped as soon as a match if obtained, and the number of eliminated subintervals is communicated to the next level of the successive dichotomy procedure, so that they do not need to be considered again at deeper levels of the recursion.

G. Figure of Merit

The system may generate thousands of possible indexing solutions, and it is advantageous to rank these solutions in such a way that the more likely candidates come first. In one embodiment, a relative figure of merit is used that takes into account the 'background noise' from incorrect indexing solutions.

One important ingredient of the relative figure of merit, $F_r$, is an absolute figure of merit, $F_a$, which may be defined as follows:

$$F_a = \frac{\bar{\theta}}{|\overline{\Delta\theta}|} \frac{N_{obs}}{N_{calc}} \frac{4.5}{N_{par}} \quad (10)$$

In the above equation, $|\overline{\Delta\theta}|$ is the average absolute difference between the calculated and the observed peak positions. The better the agreement between the two, then the higher the figure of merit is. $N_{obs}$ and $N_{calc}$ are the number of observed and the number of calculated diffraction peaks, respectively. In contrast to other indexing programs, systematic absences are explicitly taken into account and $N_{calc}$ refers to the number of present reflections. Reflections with identical 2θ values due to symmetry constrains are counted as one. The ratio $N_{obs}/N_{calc}$ in the figure of merit reflects the fact that solutions with lower numbers of calculated peaks are considered to be more reliable, because it becomes easier to fit a certain number of observed peaks if the number of calculated peaks increases. $N_{par}$ is the number of unknown parameters to be determined, including the zero-point shift and the unit cell's parameters. For triclinic, monoclinic, orthorhombic, tetragonal, hexagonal/trigonal and cubic solutions, $N_{par}$ takes the values 7, 5, 4, 3, 3 and 2, respectively. The ratio $4.5/N_{par}$ in the figure of merit reflects the fact that solutions with a low number of adjustable parameters are to be preferred, because with an increasing number of free parameters it gets more and more easy to fit a given number of observed reflections. The value 4.5 is used because it is the average of 7 and 2, although other numbers may be used as well. Finally, the incorporation of the average observed peak position, $\bar{\theta}$, in the figure of merit should be explained. Consider a set of experimental peak positions measured at a certain wavelength and an incorrect indexing solution. Ideally, the figure of merit attributed to the incorrect solution should not depend on experimental details such as the wavelength. However, as the wavelength increases, the calculated and the experimental peak positions shift to higher angles and $|\overline{\Delta\theta}|$ increases. Using $\bar{\theta}/|\overline{\Delta\theta}|$ instead of $1/|\overline{\Delta\theta}|$ in the figure approximately removes the dependency of the figure of merit on the wavelength.

The figure of merit $F_a$ has a couple of important disadvantages. First of all, it strongly depends on the number of tolerated impurity terms via the term $|\overline{\Delta\theta}|$. For a given indexing solution, the deviations between the calculated and the observed peaks will be larger for some observed peaks than for others. The more impurity peaks are allowed, the more observed peaks with large deviations from the calculated peaks can be excluded from the average $|\overline{\Delta\theta}|$, resulting in a higher figure of merit. As a consequence, solutions with a high number of unindexed reflections get relatively high rankings while solutions with a low number of unindexed reflections are to be preferred. An additional disadvantage is linked to the fact that it is not intuitively obvious what kind of values of $F_a$ to expect for promising indexing solutions.

To avoid the problems described above, the ranking in some embodiments is based on the relative figure of merit $F_r$:

$$F_r = F_a/F_{noise}(N_{obs}, N_{unindexed}) \quad (11)$$

$F_{noise}$ is an estimation of the upper limit of $F_a$ for indexing solutions that match the observed peaks accidentally and have nothing in common with the correct unit cell. The dependence of $F_{noise}$ on the number of observed reflections, $N_{obs}$, and the number of unindexed reflections, $N_{unindexed}$, has been determined empirically. From the definition of the relative figure of merit, it is intuitively clear that the most promising indexing solutions have a relative figure of merit of more than 1. Solutions with high numbers of unindexed reflections are penalized, since $F_{noise}$ increases rapidly with the number of unindexed reflections.

To determine $F_{noise}$ empirically, observed peak positions were extracted from five powder diffraction patterns and randomly modified so that there would be no correct solution. For each pattern, embodiments were run several times, taking varying numbers of observed peaks as input. The dependence of $F_{noise}$ on $N_{obs}$ and $N_{unindexed}$ was about the same in all five cases. Even though it may be desirable to repeat the parameterisation of $F_{noise}$ at some point for a larger number of powder patterns, the current parameterisation based on only five diffractograms has shown to give satisfying results in virtually all cases.

The following linbear interpolations have been used to describe the empirical dependence of $F_{noise}$ on $N_{obs}$ and $N_{unindexed}$:

Let $x = N_{unindexed}/N_{obs}$
Then $F_{noise} =$
a exp(bx) with
For $N_{obs} < 18$:  a = 900, b = 9
For $18 \leq N_{obs} < 20$: y = (20 − $N_{obs}$)/3, a = 625 + 275y, b = 6 + 3y
For $20 \leq N_{obs} < 25$: y = (25 − $N_{obs}$)/5, a = 550 + 75y, b = 5.5 + 0.5y
For $25 \leq N_{obs} < 35$: y = (35 − $N_{obs}$)/10, a = 400 + 150y, b = 4.5 + y
For $25 \leq N_{obs}$:  a = 400, b = 4.5

H. Optimization of Solutions

Throughout the optimization procedure, it is not always clear which of the observed peaks should remain unindexed. For some of the observed peaks, the calculated peaks may move further and further away, while others, first considered as impurity peaks, may be approached by calculated reflections. For the stability of the minimization procedure, it is advantageous that the expression to be minimized is a continuous function of the optimised parameters. In particular, a smooth transition between indexed and unindexed reflections should preferably be possible for all observed diffraction peaks. Therefore, instead of the figure of merit $F_a$ or $F_r$, the following expression may be optimized in some embodiments of the invention:

$$D = \sum_{obs} d_i \quad (12a)$$

$$d_i = \begin{cases} 1.0; & |Q_{obs,i} - Q_{closest,calc,i}| \geq \Delta Q_{FWHM,i} \\ |Q_{obs,i} - Q_{closest,calc,i}|/\Delta Q_{FWHM,i}; & |Q_{obs,i} - Q_{closest,calc,i}| \leq \Delta Q_{FWHM,i} \end{cases} \quad (12b)$$

In (Eq. 12a), the sum runs over all observed peaks. $Q_{obs,i}$ is the position of the i-th observed peak, while $Q_{closest,calc,i}$ is the position of the calculated reflection that is closest to the observed reflection. The system may take into account that each calculated reflection can be attributed to only one of the observed reflections. If one or more of the calculated reflections overlap with more than one observed reflection, the assignment is chosen that yields the lowest value of D. $\Delta Q_{FWHM,i}$ is the Full Width Half Maximum of the observed reflections in Q-space. If an observed reflection is more than $\Delta Q_{FWHM,i}$ away from the closest calculated reflection, it is counted as an impurity peak and contributes to D with the constant value 1.0. Otherwise, it is counted as an indexed peak and contributes a value between 0.0 and 1.0. After the minimization of D, the figures of merit $F_r$ and $F_a$ are calculated without further optimization. The average $\overline{|\Delta\theta|}$ that is part of the definition of $F_a$ is calculated by averaging over indexed reflections only.

It may happen that a calculated reflection accidentally comes close to an observed impurity peak and falls just within the cut-off value $\Delta Q_{FWHM,i}$. The impurity peak would then be counted erroneously as an indexed reflection and the relatively large distance to the calculated reflection would significantly increase the value of $\overline{|\Delta\theta|}$, resulting in a strong decrease of the figure of merit. In extreme cases, this effect may prevent the identification of the correct unit cell. To avoid this problem, some embodiments tentatively declare the observed peak with the largest deviation as an additional impurity peak and repeat the optimization of D and the calculation of $F_r$. If the value of $F_r$ goes down, the observed peak in question is considered to be an impurity peak. The procedure may be repeated until no further reduction of $F_r$ can be obtained.

I. Termination Criteria

Even when one or more solutions with fairly high figures of merit have already been found during a unit cell search, it is always possible that the correct unit cell may not yet have been generated. Therefore, unlike other indexing algorithms, embodiments of the invention may be designed to continue to look for even better solutions until the program is interrupted by the user. Typically, the user would interrupt the search when a promising solution has been confirmed as the correct unit cell by Pawley refinement or when the CPU time spent on indexing is required for other tasks.

Under certain conditions, the system may be configured to terminate automatically or stop searching in certain parts of the solution space. At each impurity level, the search terminates when the number of calculated peaks exceeds the number of observed peaks by a user-defined factor. It may also happen that the system starts finding so many solutions at a certain impurity level and in a certain crystal system that the search effectively comes to a hold. In such a case, the search in the crystal system under consideration may be stopped. However, the search may continue for all other crystal systems at the same impurity level until the search has stopped entirely at all impurity levels.

J. Long and Flat Unit Cells

Long and flat unit cells are often particularly difficult to index, because all low angle reflections belong to a single row or zone in reciprocal space, while the remaining parameters of the reciprocal lattice are defined by strongly overlapping reflections at higher 2θ values. To facilitate the indexing of long and flat unit cells, certain embodiments allow for a multi-step procedure that involves Pawley refinement.

In these embodiments, a system performing the process can be used to search for rows and zones in reciprocal space in analogy to a full unit cell search. If the first few reflections of a powder diffraction pattern are found to belong to a dominant row or zone, accurate values for the corresponding lattice parameters and the zero-point shift can be determined by Pawley refinement with a program like Reflex (Accelrys, 2001). The refined parameters and their estimated error bars can then be fed back into the system to be used in the final unit cell search. The intermediate Pawley refinement of a row or a zone has the additional advantage that it helps to identify those reflections that cannot be attributed to the dominant row or zone and thus define the remaining lattice parameters. In some embodiments, lattice parameters fed into the system are explicitly used only in the search for triclinic unit cells.

K. Unit Cell Doubling

If a crystal possesses pseudo-symmetry higher than the correct symmetry, it may happen that many allowed reflections have fairly low intensities and remain unobserved. In such cases, the correct unit cell may be hidden behind the feasibility limit, while some embodiments often can find the pseudo-symmetric cell at a high impurity tolerance level. The correct unit cell is particularly difficult to find in the special case of unit cell doubling of triclinic cells. To address the problem, some embodiments explicitly generate all triclinic cells that can be obtained from a triclinic indexing solution by unit cell doubling.

L. Input

In some systems implementing embodiments of the process described above, the systems read in an experimental data file and a parameter file as input. The experimental data file specifies the wavelength and the number of observed reflections as well as the position, FWHM and a certainty flag for each reflection. The certainty flag indicates whether or not an observed reflection may be treated as an impurity peak.

In the parameter file, the user can specify whether to search for a row, a zone or a unit cell. If a unit cell search is performed, the user can decide which crystal systems to search in. The user can also set the highest allowed impurity tolerance level and decide if the search should be carried out at the highest allowed impurity tolerance level only or in parallel at all levels up to the allowed maximum. The highest allowed number of calculated peaks is set via the specification of the lowest possible detection ratio. The detection ratio is defined here as the number of observed peaks divided by the number of calculated peaks. Finally, it is possible to enter the allowed range of the zero-point shift and, optionally, one or three lattice parameters with error bars.

M. Output

For each indexing solution found, the system may provide the user with the figures of merit $F_r$ and $F_a$, the average deviation $\overline{|\Delta\theta|}$, the unit cell volume, the crystal system, a space group as the representative of a powder extinction class, a stability parameter, the number of unindexed reflections, the number of observed peaks, the number of calculated peaks that do not overlap with observed peaks, the total number of calculated peaks, the lattice parameters and the zero-point shift. The stability parameter approximately indicates the minimum number of observed reflections that have to be removed so that the unit cell is no longer uniquely defined.

In one embodiment, two lists of up to 5000 indexing solutions are compiled, the solutions being ranked according to the figure of merit $F_r$. One of the lists, intended to provide input for further automatic processing, contains all indexing solutions down to a certain figure of merit. Identical unit cells found in different powder extinction classes are counted as separate solutions. The second list is meant to provide a limited number of solutions for individual examination. Only solutions with a relative figure of merit and a stability parameter of at least 2 are incorporated in this list. If a unit cell is found in several powder extinction classes, only the solution with the highest figure of merit is added to the list.

Certain embodiments thus include methods of indexing powder diffraction data that include one or more of the advantageous acts described above. The invention further includes systems comprising a general-purpose computer, which is configured with one or more software modules to perform on or more of the acts described above. The general purpose computer will typically include a memory storing instructions and a memory storing diffraction data which is retrieved and processed in accordance with the advantageous methods described above. The invention also includes computer readable media having instructions stored thereon which cause a general purpose computer to perform one or more of the acts described above.

N. Computer System

Figure 3:
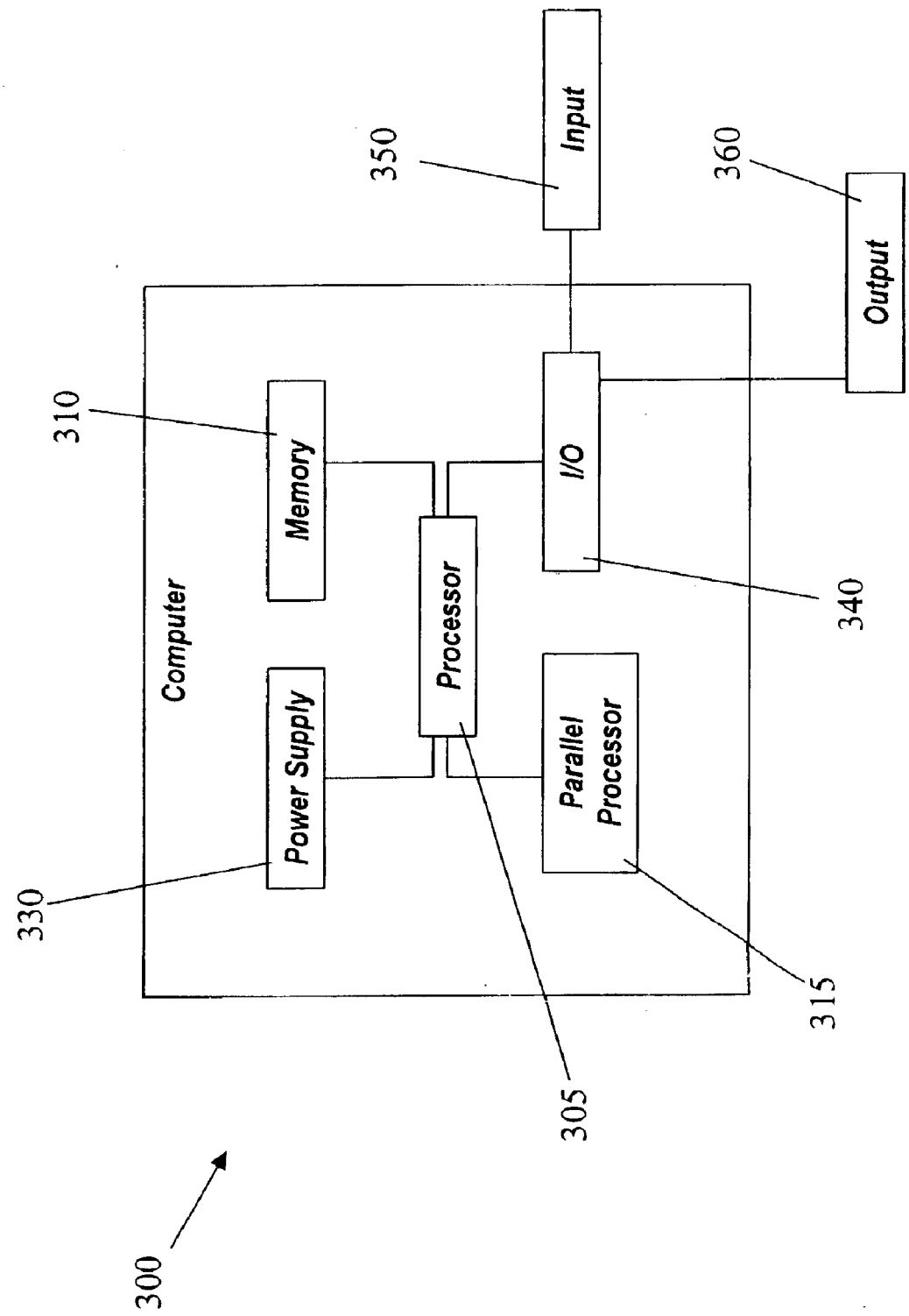
FIG. 3 is a schematic diagram illustrating a computer system of one embodiment that can perform the indexing process.

Referring to FIG. 3, an embodiment of a computer system 300 or data processing station is illustrated that is capable of receiving data, storing the data, and processing the data as described above. In the following description, the computer system 300 is assumed to have all connectivity necessary to fulfill and embody the functions that will be described including all communication ports and connections as well as any required conductors and bus-work. The computer system 300 is comprised of various modules 305-360. As can be appreciated by one of ordinary skill in the art, each of the modules 305-360 comprises various sub-routines, procedures, definitional statements, and macros. Each of the modules 305-360 can be separately compiled and linked into a single executable program, or alternatively could be compiled into a plurality of executable programs. Therefore, the following description of each of the modules 305-360 is used for convenience to describe the functionality of the computer system 300. Thus, the processes that are undergone by each of the modules 305-360 may be arbitrarily redistributed to one of the other modules, combined together in a single module, or made available in a shareable dynamic link library. Furthermore, the organization of the various functional modules in the structure illustrated in FIG. 3 is provided merely for illustrative purposes only and the modules can be organized in any other way and can be located in different structures than the one illustrated here. In some embodiments, many of the components can be located in one housing or in multiple structures.

Still referring to FIG. 3, the main operative module of the computer system 300 is a processor 305. The various illustrative logical blocks, modules, and circuits described in connection with the embodiments disclosed herein, may be implemented or performed with or by the processor 305, which can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor 305 may be a microprocessor, but in the alternative, the processor 305 may be any processor, controller, microcontroller, or state machine. The processor 305 may also be implemented as a combination of computing devices, for example, a combination of a DSP and a microprocessor, a plurality of microprocessors, one or more microprocessors in conjunction with a DSP core, or any other such configuration. In some embodiments, the processor 305 may be any conventional general purpose single or multi-chip microprocessor such as a Pentium® processor or its progeny, a AMD Athlon® or its progeny, an Itanium® 64-bit processor or its progeny, a MIPS® processor, a PowerPC® processor or its progeny, or an ALPHA® processor or its progeny. In addition, the processor 305 may be any conventional special purpose microprocessor such as a digital signal processor as described above.

Additionally, the computer system 300 has a memory 310 for storing data and other information. The memory 310 may include any storage medium including, but not limited to, RAM memory, DRAM memory, SDRAM memory, flash memory, ROM memory, EPROM memory, EEPROM memory, registers, hard disk, a removable disk, a CD-ROM, a DVD-ROM, or any other form of storage medium. An exemplary storage medium, or memory 310, is coupled to the processor 305 such that the processor 305 can read information from, and write information to, the memory 310. In the alternative, the memory may be integral with the processor 305. The processor 305 and the memory 310 may reside in an ASIC.

Still referring to FIG. 3, the processor 305 performs analysis functions on the data received and stored in the memory 310, and some embodiments utilize a parallel processor or coprocessor 315, such as a floating point accelerator or any other parallel processor, to assist in the performance of many of these analytical functions. In many embodiments, the computer system 300 has an input/output module (I/O) 340 for controlling information coming into and out of the computer system 300. The I/O 340 receives commands that operate the computer system 300 from an input source 350. For example, the input source 350 can be a keyboard, trackball, pen and stylus, mouse, digitizer, or voice recognition system, but can also be a connection to a network (not shown) or other connection such as a USB port, a Serial port, a Parallel port, a Fire Wire port, a disc drive, or other data input means. The input source 350 can also be a touch screen associated with an output device 1060. The user may respond to prompts on the display by touching the screen. The user may enter textual or graphic information along with data through the input device that represents command subroutines to be executed by the computer system 300. The output signals from the computer system 300 are sent to an output device 360, or system, for use by the operator. The output device 360 can be a printer, a plotter, a display for graphic output, or an audio output for sound or voice synthesis, or it can be a connection to a server or a network, such as a LAN, a WAN, or the Internet, or it can be any other form as required by the operator.

In some embodiments, the computer system of FIG. 3 advantageously programmed to perform the methods described above in a diffraction data indexing process. Diffraction data is retrieved or otherwise input to the system, and the processor performs one or more of the above described methods. Indexing solutions are then output to the user of the system.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of indexing powder diffraction data, comprising:

choosing a maximum impurity peak tolerance level to limit the search for indexing solutions to those where the number of unindexed peaks lies within the tolerance level;

choosing a range for the number of calculated peaks to limit the search for indexing solutions to those where the number of calculated peaks falls within the chosen range;

selecting a crystal system to search;

selecting a powder extinction class to search for indexing solutions; and performing a unit cell search of the selected powder extinction class using a successive dichotomy approach to determine a set of indexing results.

2. A method for exploiting space group symmetry in the indexing of powder diffraction data, by selecting a crystal system to search, then grouping possible indexing solutions compatible with this crystal system into powder extinction classes having the same pattern of systematic absences, and performing separate indexing solution searches within at least two of said powder extinction classes.

3. The method of claim 2, wherein said separate indexing solution searches are performed with a successive dichotomy method.

4. The method of claim 2, wherein said separate indexing solution searches are limited to searching for solutions having a preselected maximum number of calculated reflections.

5. A system for indexing a set of powder diffraction data, comprising: a general purpose processor, wherein the processor is configured to divide the data into a plurality of powder extinction classes having the same pattern of systematic absences, and wherein the processor is further adapted to search each powder extinction class over a calculated peak number range.

6. A system for indexing a set of powder diffraction data, comprising:

a memory storing diffraction data; and at least one processor configured to read data from and write data to the memory and further configured to analyze said data to produce indexing solutions starting at solutions with a small number of calculated peaks and progressing toward solutions with a larger number of calculated peaks.

7. The system of claim 6, wherein said processor is configured to perform a series of separate successive dichotomy searches using a corresponding series of calculated peak number ranges.

8. A method of analyzing diffraction data comprising:

generating a plurality of indexing solutions from said diffraction data;

ranking said indexing solutions by calculating a figure of merit for at least some of said indexing solutions, wherein said figure of merit is constructed such that it tends to rank solutions with smaller numbers of calculated reflections higher.

9. The method of claim 8, wherein said figure of merit comprises the expression $N_{obs}/N_{calc}$, wherein $N_{obs}$ is the number of measured reflections in said diffraction data, and $N_{calc}$ is the number of calculated reflections for the ranked indexing solution.

10. The method of claim 8, wherein said figure of merit tends to rank highly solutions with a smaller number of fitted parameters.

11. The method of claim 8, wherein said figure of merit $F_a$ is of the form:

$$F_a \propto \frac{\bar{\theta}}{|\overline{\Delta\theta}|} \frac{N_{obs}}{N_{calc}} \frac{1}{N_{par}}$$

wherein $N_{obs}$, is the number of measured reflections in said diffraction data, and $N_{calc}$ is the number of calculated reflections for the ranked indexing solution, $N_{par}$ is the number of fitted parameters producing the solution, $\bar{\theta}$ is average observed peak position, and $|\overline{\Delta\theta}|$ is the average absolute difference between the calculated and the observed peak positions.

12. The method of claim 11, additionally comprising normalizing said figure of merit relative to an approximate expected average figure of merit produced from a randomly selected incorrect indexing solution.

13. A system for indexing powder diffraction data, comprising:

means for choosing a maximum impurity peak tolerance level for a crystallography data search;

means for choosing a range of number of calculated peaks for possible indexing solutions having a minimum number of peaks and a maximum number of peaks;

means for selecting a crystal system to search;

means for selecting a powder extinction class to search for indexing solutions; and means for performing an exhaustive unit cell search of the selected powder extinction class using a successive dichotomy approach to determine a set of indexing results.

14. The apparatus of claim 12, additionally comprising means for ranking and comparing indexing solutions for powder diffraction data corresponding to different extinction classes using a figure of merit designed to rank highly the most likely solutions.

* * * * *